US010231755B2

(12) United States Patent
Brown et al.

(10) Patent No.: US 10,231,755 B2
(45) Date of Patent: Mar. 19, 2019

(54) APPARATUS INCLUDING A CYLINDRICAL BODY AND A NUB

(71) Applicants: Maureen Brown, Austin, TX (US); Marc Brown, Austin, TX (US)

(72) Inventors: Maureen Brown, Austin, TX (US); Marc Brown, Austin, TX (US)

(*) Notice: Subject to any disclaimer, the term of this patent is extended or adjusted under 35 U.S.C. 154(b) by 476 days.

(21) Appl. No.: 14/272,368

(22) Filed: May 7, 2014

(65) Prior Publication Data

US 2015/0320443 A1  Nov. 12, 2015

(51) Int. Cl.
A61B 17/43 (2006.01)
A61D 19/02 (2006.01)
A61M 5/31 (2006.01)

(52) U.S. Cl.
CPC ............ *A61B 17/43* (2013.01); *A61D 19/027* (2013.01); *A61M 5/3134* (2013.01)

(58) Field of Classification Search
CPC ....... A61J 1/2086; A61D 19/027; A61B 17/43
USPC .......................................................... 600/33
See application file for complete search history.

(56) References Cited

U.S. PATENT DOCUMENTS

| 2,514,575 A | 11/1950 | Hein |
| 2,688,968 A * | 9/1954 | Scherer .................... A61M 5/30 604/72 |
| 4,043,334 A * | 8/1977 | Brown ................. A61M 5/3134 604/199 |
| 4,287,888 A | 9/1981 | Schwarz |
| 5,084,004 A | 1/1992 | Ranoux |
| 5,147,315 A | 9/1992 | Weber |
| 5,259,836 A | 11/1993 | Thurmond |
| 5,266,071 A | 11/1993 | Elftman |
| 5,472,419 A | 12/1995 | Bacich |
| 5,496,272 A | 3/1996 | Chung |
| 5,531,709 A | 7/1996 | Eykmann et al. |
| 5,536,234 A | 7/1996 | Newman |
| 5,858,354 A | 1/1999 | Brinster |
| 5,904,665 A | 5/1999 | Muharib |
| 5,944,698 A * | 8/1999 | Fischer ............... A61M 5/3134 604/236 |
| 5,967,368 A | 10/1999 | Guillermier |
| 6,264,638 B1 | 7/2001 | Contente |
| 6,551,236 B1 | 4/2003 | Liegois |
| 6,699,226 B2 | 3/2004 | Velazquez |
| 6,890,708 B2 | 5/2005 | Matthijs-Rijsenbilt |
| RE39,533 E | 3/2007 | Ranoux |
| 7,282,363 B1 | 10/2007 | Ranoux |

(Continued)

FOREIGN PATENT DOCUMENTS

WO    2013038166    3/2013

OTHER PUBLICATIONS

Search Report and Written Opinion, PCT/US2015/029310, dated Aug. 27, 2015, 7 pages.

(Continued)

*Primary Examiner* — Christine H Matthews
(74) *Attorney, Agent, or Firm* — Matthew Burr

(57) ABSTRACT

An apparatus includes a substantially cylindrical body including an end portion having rounded edges and at least one opening. The apparatus further includes a nub integrally formed with the substantially cylindrical body and extending from the end portion proximate to the at least one opening. The nub includes a substantially rounded end.

18 Claims, 6 Drawing Sheets

(56) References Cited

U.S. PATENT DOCUMENTS

| | | |
|---|---|---|
| 7,344,492 B2 | 3/2008 | Ainley |
| 7,419,465 B2 | 9/2008 | Ainley |
| 7,666,160 B2 | 2/2010 | Rajala |
| 7,759,115 B2 | 7/2010 | Etheredge |
| 7,837,611 B2 | 11/2010 | Ainley |
| 8,323,178 B2 | 12/2012 | Ainley |
| 2002/0198498 A1 | 12/2002 | Porat et al. |
| 2004/0006291 A1 | 1/2004 | Rehrig |
| 2006/0074273 A1 | 4/2006 | Smith |
| 2006/0122563 A1 | 6/2006 | Ziv |
| 2009/0326479 A1* | 12/2009 | Janish ................ A61M 5/31511 604/218 |
| 2011/0034868 A1* | 2/2011 | Eichhorst ................ A61M 5/30 604/68 |
| 2011/0224648 A1 | 9/2011 | Secci |
| 2013/0090629 A1 | 4/2013 | Cant |
| 2013/0217961 A1 | 8/2013 | Godden |
| 2014/0046127 A1 | 2/2014 | Topolovac |
| 2014/0107410 A1 | 4/2014 | Rosenberg |
| 2014/0309488 A1 | 10/2014 | Fowler |

OTHER PUBLICATIONS

Suarez, Sperm Transport in the Female Reproductive Tract, Human Reproduction Update, vol. 12, No. 1 pp. 23-37, 2006.

Abou-Setta, Intrauterine insemination catheters for assistedreproduction: a systematic review and meta-analysis, Human Reproduction vol. 21, No. 8 pp. 1961-1967, 2006.

* cited by examiner

APPARATUS INCLUDING A CYLINDRICAL BODY AND A NUB

FIELD

The present disclosure is generally related to a fluid dispensing apparatus, and more particularly to an apparatus including a substantially cylindrical body and a nub, where the cylindrical body and the nub are rounded.

BACKGROUND

Infertility is a common problem among couples. An evaluation by a doctor is often recommended after a period of time (such as one year) of unprotected intercourse without achieving conception. While it is sometimes possible to identify correctable issues that may be preventing conception, some couples pursue expensive medical solutions, such as in vitro fertilization at a fertility clinic.

SUMMARY

In an embodiment, an apparatus includes a substantially cylindrical body including an end portion having rounded edges and at least one opening. The apparatus further includes a nub extending from the end portion proximate to the at least one opening. The nub includes a substantially rounded end.

In another embodiment, an apparatus includes a cylindrical body having a proximal end, a distal end and an elongate portion extending therebetween. The distal end has a rounded corner relative to the elongate portion to form a substantially smooth transition from the elongate portion to the distal end. The distal end further includes an opening. The apparatus further includes a nub coupled to and extending from the distal end proximate to the opening. The nub has a rounded end.

In still another embodiment, an apparatus includes a tubular element including a body portion and a distal end and including a substantially smooth surface having rounded edges. The distal end includes an opening. The apparatus further includes a nub extending from the distal end proximate to the opening and having a substantially rounded shape.

BRIEF DESCRIPTION OF THE DRAWINGS

In the following discussion, the same reference numbers are used in the various embodiments to indicate the same or similar elements.

DETAILED DESCRIPTION OF ILLUSTRATIVE EMBODIMENTS

Embodiments of an apparatus are disclosed below that include a substantially cylindrical body portion and a nub that extends from a distal end of the body portion. The cylindrical body portion may be a syringe, a sheath sized to receive a syringe, or cap configured to couple to a syringe. The nub may have a rounded shape, such as a hemispherical shape, a ring shape (with rounded edges), an elliptical shape (with rounded edges), a bulbous shape, or some other rounded shape. In some embodiments, the nub may have a diameter that is less than a cross-sectional diameter of the syringe. Further, the edges of the syringe, the sheath, the cap, or any combination thereof, may be rounded, presenting a smooth transition from the elongate body portion to the distal end. In some embodiments, portions of the syringe, portions of the cap, portions of the sheath, or any combination thereof may be formed from a first material, while other portions of the syringe, the sheath, the cap, or any combination thereof may be formed from a second material. In some embodiments, the second material may be more flexible or malleable than the first material.

In some embodiments, the apparatus may be used for artificial insemination by filling a fluid canal of a barrel of the syringe with seminal fluid, and by inserting the apparatus into the vaginal canal to deliver seminal fluid through the vaginal canal to the cervix of the woman. The nub may provide tactile feedback to the woman by allowing her to feel when the distal end of the apparatus is touching the cervix. Further, the feedback provided by the nub may allow the woman to adjust the position of the apparatus relative to the cervix prior to depression of the plunger of the syringe to deliver of the seminal fluid. Embodiments of the apparatus are described below with respect to FIGS. 1-13.

Figure 1:
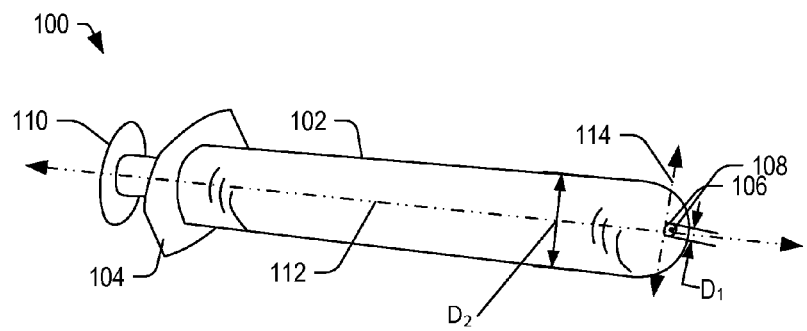
FIG. 1 is a perspective view of an apparatus including a syringe with a nub according to some embodiments.

FIG. 1 is a perspective view of an apparatus 100 including a syringe 102 with a nub 106 according to some embodiments. The syringe 102 may include a body having a proximal end with a flange 104 and may define a cavity sized to receive a plunger 110 to draw fluid into the cavity and to propel fluid through the opening 108. The flange 104 may be used as leverage by a user when depressing the plunger 110. Further, the body of the syringe 102 may include a distal end with the nub 106. The distal end of the body of the syringe 102 may also include an opening 108 to allow fluid flow. In the illustrated example, the opening 108 extends through a corresponding opening in the nub 106; however, it should be understood that the nub 106 and the opening 108 may be offset from one another. In some embodiments, the opening 108 may be offset from a center of the distal end of the syringe 102. In some embodiments, the nub 106 may be offset from the center of the distal end. In some embodiments, the nub 106 and the opening 108 may be offset from the center of the distal end.

In some embodiments, the body of the syringe 102 may have a substantially cylindrical shape (or tubular shape) forming a fluid conduit and having rounded edges at the distal end. Further, the nub 106 may have a substantially semi-spherical shape and may extend outward from the distal end of the syringe 102 proximate to a longitudinal axis 112 of the syringe 102. In some embodiments, the nub 106 may have a diameter ($D_1$) that is orthogonal to the longitudinal axis 112 of the syringe 102 and that is smaller than a diameter ($D_2$) of the body of the syringe 102.

In some embodiments, a user may draw fluid into a cavity within the body of the syringe 102 by pulling the plunger 110. The user may then insert the syringe 102 into the vaginal cavity and depress the plunger 110 to dispense the fluid through opening 108. The nub 108 may provide feedback to the woman to allow her to feel the position of the distal end of the syringe 102 against her cervix prior to dispensing the fluid.

In some embodiments, the rounded edges of the distal end of the body of the syringe 102 and the rounded shape of the nub 108 provide a substantially smooth and relatively comfortable feel as compared to a standard syringe that has corners and a pointed (though needle-less) end. While a conventional syringe may have edges or corners that can be sharp or abrasive, the syringe 102 and the nub 108 are rounded to provide smooth edges.

While the illustrated example of FIG. 1 included a single opening that extends through the nub 108, it should be understood that the distal end of the syringe 102 may include one or more openings to allow fluid passage to and from the cavity within the body of the syringe 102 and the outside environment. One possible example of a syringe that includes multiple openings is described below with respect to FIG. 2.

Figure 2:
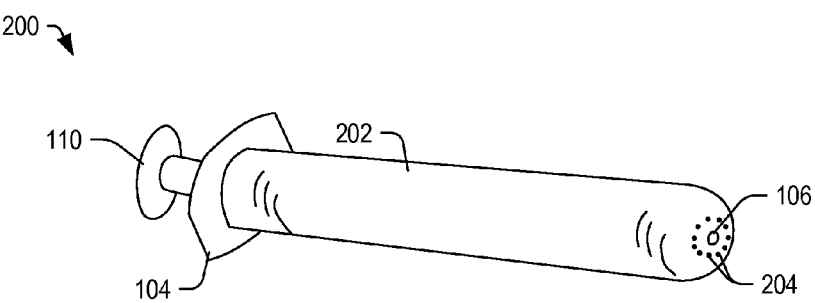
FIG. 2 is a perspective view of an apparatus including a syringe with a nub according to some embodiments.

FIG. 2 is a perspective view of an apparatus 200 including a syringe 202 with a nub 106 according to some embodiments. The syringe 202 includes the flange 104 and includes a cavity sized to receive the plunger 110. The syringe 202 further includes multiple openings 204 extending from the cavity to the outside environment. In the illustrated example, the openings 204 are distributed about the nub 106 and are offset from the nub 106. In some embodiments, additional openings 204 or fewer openings may be provided. In some embodiments, the openings 204 may be distributed circumferentially along the sidewalls of the body of the syringe 202 near the distal end. Further, in some embodiments, the openings 204 may align with corresponding openings that extend through the nub 106.

In the illustrated examples of FIGS. 1 and 2, the syringe 102 and 202 may be formed from a first material, such as a substantially rigid, anti-bacterial and anti-microbial plastic material, while the nub 106 may be formed from a second material, that may also have anti-bacterial and anti-microbial properties, but that may be more elastic or malleable than the first material. Additionally, in some embodiments, the nub 106 may be attached to or coupled to the syringe 102, 202. In some embodiments, the nub 106 may be integrally formed with the syringe 102, 202. An example of some embodiments of the syringe 202 having an integrally formed nub 106 and including the opening 108 is described below with respect to FIG. 3.

Figure 3:
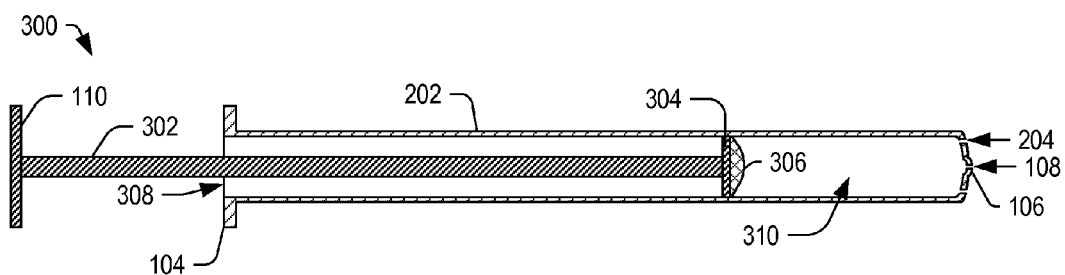
FIG. 3 is a cross-sectional view of an apparatus including a syringe with a nub according to some embodiments.

FIG. 3 is a cross-sectional view of an apparatus 300 including a syringe 202 with a nub 106 according to some embodiments. The syringe 202 includes a body portion that defines a cavity 308 that extends from a proximal end, which includes the flange 104, to a distal end, which includes openings 204, and the nub 106. Additionally, in some embodiments, the nub 106 also includes an opening 108. The openings 108 and 204 extend through the distal end of the body of the syringe 202 to permit fluid flow between a fluid area 310 and the environment.

The apparatus 300 further includes the plunger 110 including a rod portion 302 and an end portion 304. A gasket or seal 306 may be coupled to the end portion 304 to provide a fluid seal to prevent fluid flow from the fluid area 310 toward the body portion 302 and to draw fluid through the openings 108 and 204 in to the fluid area 310 or to drive fluid from the fluid area 310 through the openings 108 and 204.

In some embodiments, the nub 106 may be part of the distal end of the body of the syringe 202. In some embodiments, the nub 106 may omit the opening 108 and the openings 204 may be included. In some embodiments, the openings 204 may be omitted and the opening 108 may be included.

In some embodiments, an outer sheath or covering may be provided that may be adapted to cover a needle-less syringe. The outer sheath may be configured to receive the syringe and to provide a rounded distal end and a nub. An example of an apparatus including a sheath is described below with respect to FIGS. 4-10 according to some embodiments.

Figure 4:
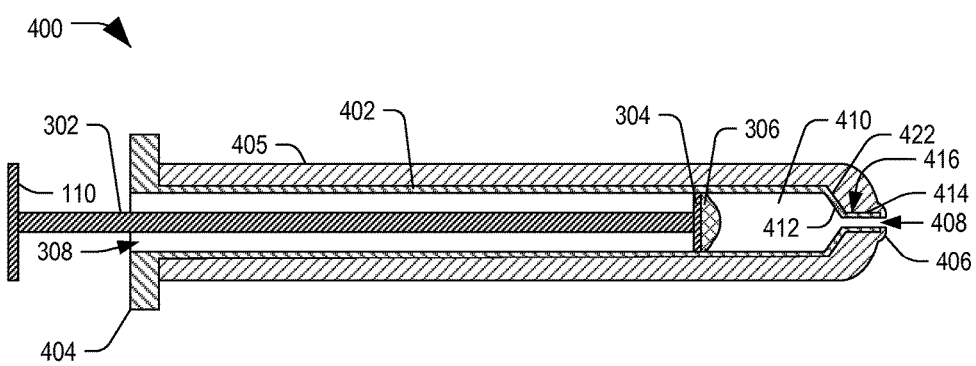
FIG. 4 is a cross-sectional view of an apparatus including a syringe and a sheath including a nub according to some embodiments.

FIG. 4 is a cross-sectional view of an apparatus 400 including a syringe 402 and a sheath 405 including a nub 406 according to some embodiments. The syringe 402 includes a body portion defining the cavity 308 sized to receive a plunger 110 having a rod portion and an end portion 304 that is coupled to a gasket or seal 306. The syringe 402 may further include a flange 404, a hub portion 412, and a nose portion 414. The nose portion 414 may define an opening for fluid passage from a fluid area 410 and the external environment.

The sheath 405 may include a stop portion 422 configured to contact the hub portion 212 of the syringe 402 to seat the syringe 402 within the sheath 405. The sheath may be a substantially cylindrical (or tubular member) defining a cavity sized to receive the syringe 402. The sheath 405 may also include an opening 416 configured to receive the neck portion 414 of the syringe 402. The sheath 405 may further includes a nub 406 that extends outward from a distal end of the sheath 405. The nub 406 may have a rounded, substantially hemispherical, ring, elliptical, or other rounded shape that may partially define the opening 416 that is configured to align with a corresponding opening 108 through the neck portion 414 to allow fluid passage.

In some embodiments, the sheath 405 may be formed from a first material, and the syringe 402 may be formed from a second material. The first material may be more elastic, more malleable, softer, or any combination thereof relative to the second material. In some embodiments, the sheath 405 may have a substantially cylindrical shape without edges and may define an opening on a proximal end that is sized to receive a syringe 402. The sheath 405 may include one or more openings configured to align with an opening on the syringe. Further, in some embodiments, the surface of the sheath 405 may have some texture or uneven areas. Additionally, in some embodiments, the sheath 405 may include an attachment element, such as threads to mate with corresponding threads on an outer surface of a syringe, a flange element configured to mate with a corresponding recess on the syringe, some other attachment structure, or any combination thereof. An example of a sheath that includes an attachment structure is described below with respect to FIG. 5.

Figure 5:
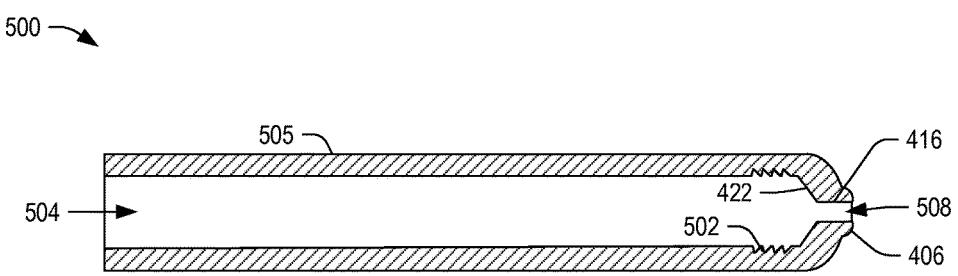
FIG. 5 is a cross-sectional view of a sheath including a nub and a threaded attachment according to some embodiments.

FIG. 5 is a cross-sectional view 500 of a sheath 505 including a nub 406 and a threaded attachment 502 according to some embodiments. The sheath 505 may define a cavity 504 sized to receive a syringe and may include an opening 508 configured to align to a corresponding opening 408 of a syringe. The sheath 505 further includes an attachment feature 502. In the illustrated example, the attachment feature 502 may be threads configured to fit corresponding threads on an exterior surface of the syringe. The user may turn the syringe within the cavity 504 in order to secure the sheath 505 to the syringe.

In some embodiments, the size of the opening 416 may be sufficiently narrow to apply a hoop stress on the neck portion 414 of the syringe 402 to secure the sheath 505 to the syringe. In some embodiments, an extension on an inner surface of the sheath 505 may be configured to mate with a corresponding recess on an exterior surface of the syringe to secure the sheath 505 to the syringe.

In some embodiments, the sheath 505 may be formed from a medical grade silicone. In some embodiments, the sheath 505 may be formed from a medical device material, such as a polymer designed to support medical applications and to maintain its material properties even after sterilization. In some embodiments, the sheath 505 may be formed from a flexible, substantially malleable material that may be of a different material from that of the syringe.

Figure 6:
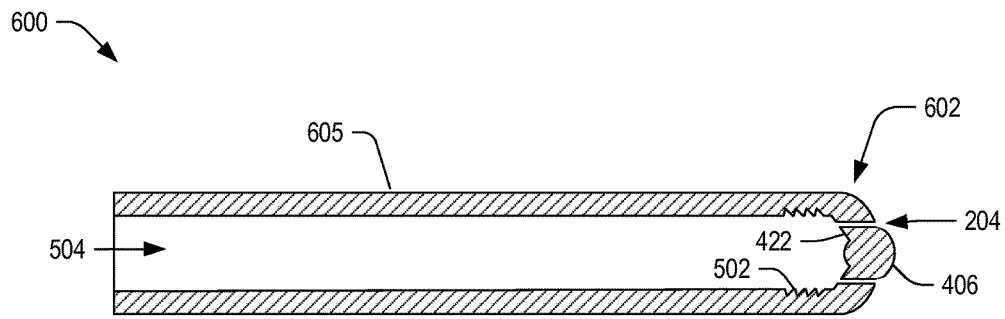
FIG. 6 is a cross-sectional view of a sheath including a nub and a threaded attachment according to some embodiments.

FIG. 6 is a cross-sectional view 600 of a sheath 605 including a nub 406 and a threaded attachment 502 according to some embodiments. The sheath 605 defines a cavity 504 sized to receive a syringe and includes a threaded feature 502 configured to mate with a corresponding feature on an outside surface of the syringe to secure the syringe within the sheath 605. The sheath 605 includes a nub 406 that extends from a distal end 602 of the sheath 605. The sheath 605 includes openings 204 about a periphery of the nub 406.

Figure 7:
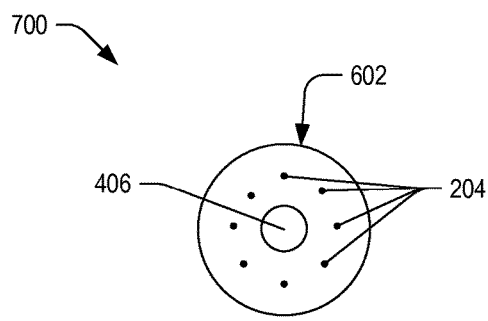
FIG. 7 is a front view of a distal end of the sheath of FIG. 6 according to some embodiments.

FIG. 7 is a front view 700 of a distal end 602 of the sheath 605 of FIG. 6 according to some embodiments. The distal end 602 includes openings 204 and nub 406. While the openings 204 are distributed around the nub 406 of the distal end 602 approximately midway between the nub 406 and the peripheral edge of the distal end 602, in some embodiments, the openings 204 may be positioned closer to the peripheral edge or closer to the nub 406. Further, in some embodiments, additional openings or fewer openings may be provided. One possible example of a distal end that includes an additional opening is described below with respect to FIG. 8.

Figure 8:
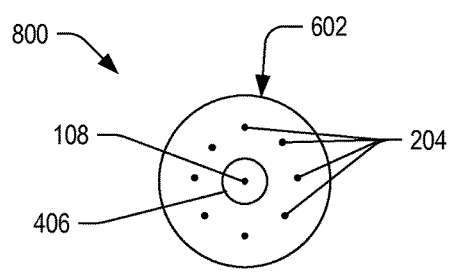
FIG. 8 is a front view of a distal end of a sheath, similar to the sheath of FIG. 6 according to some embodiments.

FIG. 8 is a front view 800 of a distal end 602 of a sheath, similar to the sheath 605 of FIG. 6, according to some embodiments. The front view 800 includes the opening 108 that extends through a center of the nub 406 in addition to the openings 204.

In some embodiments, the nub 406 may be positioned at approximately a center of the distal end 602. In some embodiments, the nub 406 may be offset from a center of the distal end 602. The opening 108 may be aligned to a longitudinal axis of a syringe.

Figure 9:
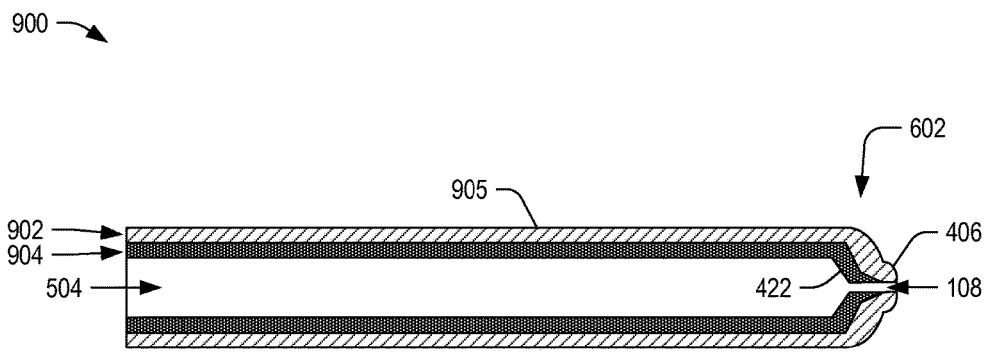
FIG. 9 is a cross-sectional view of a sheath including a nub according to some embodiments.

FIG. 9 is a cross-sectional view 900 of a sheath 905 including a nub 406 according to some embodiments. The sheath 905 may include multiple layers including an outer layer 902 and an inner layer 904. The sheath 905 may define an opening 504 sized to receive a syringe. The outer layer 902 may include the nub 406. In some embodiments, the inner layer 904 and the outer layer 902 may cooperate to form the nub 406. In some embodiments, the inner layer 904 may be formed from a first material and the outer layer 902 may be formed form a second material. In some embodiments, the first material may be more rigid than the second material.

While the illustrated example of FIG. 9 depicts the inner layer extending from the opening of the proximal end along its entire length to the opening of the distal end 602, in some embodiments, the inner layer may extend only a portion of the length of the sheath 905. One possible example of a sheath having an inner layer that extends for only a portion of the length of the sheath is described below with respect to FIG. 10.

Figure 10:
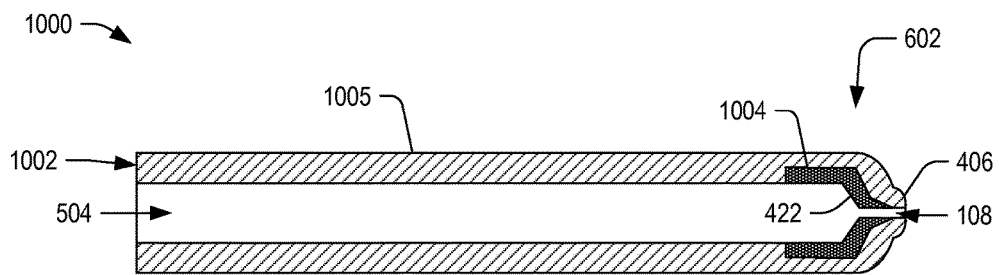
FIG. 10 is a cross-sectional view of a sheath including a nub according to some embodiments.

FIG. 10 is a cross-sectional view 1000 of a sheath 1005 including a nub 406 according to some embodiments. The sheath 1005 may include multiple layers including a first layer 1002 that extends about an entire periphery of the sheath 1005. The sheath 1005 may further include an inner layer 1004 that extends over a portion of an interior surface of the sheath 1005. In some embodiments, the inner layer 1004 may extend over the stop portion 422 of the sheath 1005, providing a relatively rigid seat against which the syringe may be positioned without over-stressing the distal end 602 of the sheath 1005.

In some embodiments, the nub 406 may include an opening that extends therethrough, and the nub 406 may be positioned at approximately a center of the distal end 602. In some embodiments, the nub 406 may be offset from a center axis of the sheath 1005. In some embodiments, the nub 406 may extend at least partially over the opening 108 to prevent the fluid from dispensing in a direct stream out of the opening 108, and dispersing the fluid over a larger spray area than a fluid stream would otherwise provide.

While the embodiments described above included a syringe with a nub and a sheath with a nub, in some embodiments, the nub may be provided on a cap configured to fit onto a distal end of a syringe. Examples of such embodiments are described below with respect to FIGS. 11-14.

Figure 11:
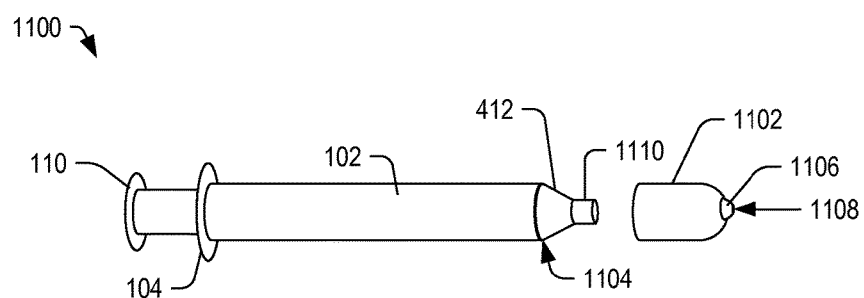
FIG. 11 is a side view of an apparatus including a syringe and a cap including a nub according to some embodiments.

FIG. 11 is a side view of an apparatus 1100 including a syringe 102 and a cap 1102 including a nub 1106 according to some embodiments. The syringe 102 includes the plunger 110 and the flange 104. The syringe 102 may further include a hub portion 412 and a neck portion 1110 that extends from the hub portion 412 and through which the opening 108 may extend. The syringe 104 may further include an attachment feature 1104 configured to mate with a corresponding attachment feature of the cap 1102.

In some embodiments, the cap 1102 may be a substantially cylindrical shape (or tubular shape) having a rounded end that includes a nub 1106 and an opening 1108 that extends through the cap 1102. The cap 1102 may include an attachment feature on an interior surface of the cap 1102 that may be configured to couple to the attachment feature 1104 on the syringe 102 to secure the cap 1102 to the syringe 102. In some embodiments, the cap 1102 includes an opening 1108 configured to align to the opening 108 of the neck 1110 of the syringe 102.

Figure 12:
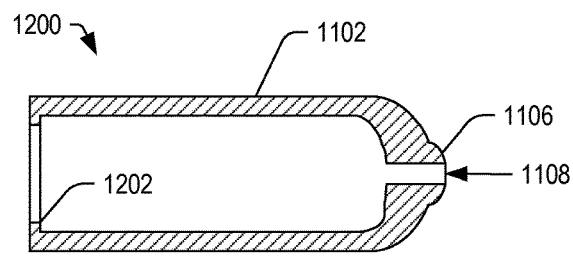
FIG. 12 is a cross-sectional view of the cap of FIG. 11 including an attachment mechanism according to some embodiments.

FIG. 12 is a cross-sectional view 1200 of the cap 1102 of FIG. 11 including an attachment mechanism 1202 according to some embodiments. The attachment mechanism 1202 may be configured to mate with a corresponding recess 1104 of the syringe 102 in a manner that may be similar to a pen cap coupling to a pen. In some embodiments, the attachment feature 1202 may be a flange or other structure that extends from an inner surface of the cap 1102. In some embodiments, the attachment feature 1202 may extend about an entire inner circumference of the cap 1102. In some embodiments, the attachment feature 1202 may extend about a portion of the inner circumference of the cap 1102.

Figure 13:
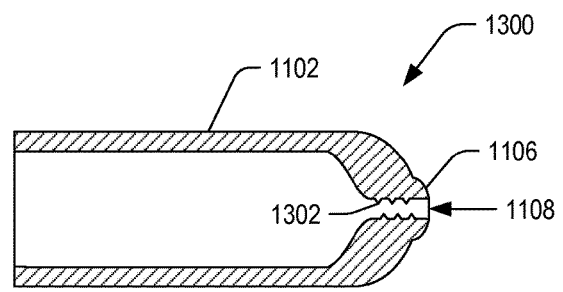
FIG. 13 is a cross-sectional view of the cap of FIG. 11 including an attachment mechanism according to some embodiments.

FIG. 13 is a cross-sectional view 1300 of the cap 1102 of FIG. 11 including an attachment mechanism 1302 according to some embodiments. In some embodiments, the attachment mechanism 1302 may be located at a stop portion of the cap 1102. In some embodiments, the attachment mechanism 1302 may be located within an opening 1108 of the cap 1102. The attachment mechanism 1302 may be a threaded portion configured to mate with a corresponding threaded portion of a syringe to secure the cap 1102 to the syringe.

While the cap 1102 depicted in FIGS. 11-13 includes the opening 1108 located at a center of the rounded end of the cap 1102, it should be appreciated that, in some embodiments, the opening 1108 may be offset from a center axis of the cap 1102. In some embodiments, the cap 1102 may include multiple openings as described below with respect to FIG. 14.

Figure 14:
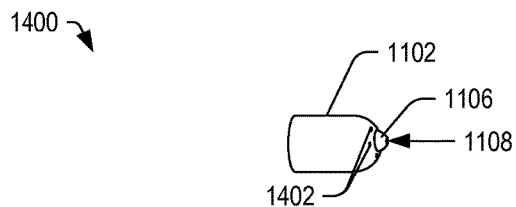
FIG. 14 is a side view of a cap configured to couple to a syringe according to some embodiments.

FIG. 14 is a side view 1400 of a cap 1102 configured to couple to a syringe according to some embodiments. The cap 1102 includes a nub 1106 and an opening 1108 that extends through the nub 1106. Additionally, the cap 1102 includes multiple openings 1402, which may be arranged circumferentially about the nub 1106. Within the cap 1102, the openings 1402 may be coupled to an opening 108 of the syringe by conduits extending from the opening 108 to the openings 1402.

Figure 15:
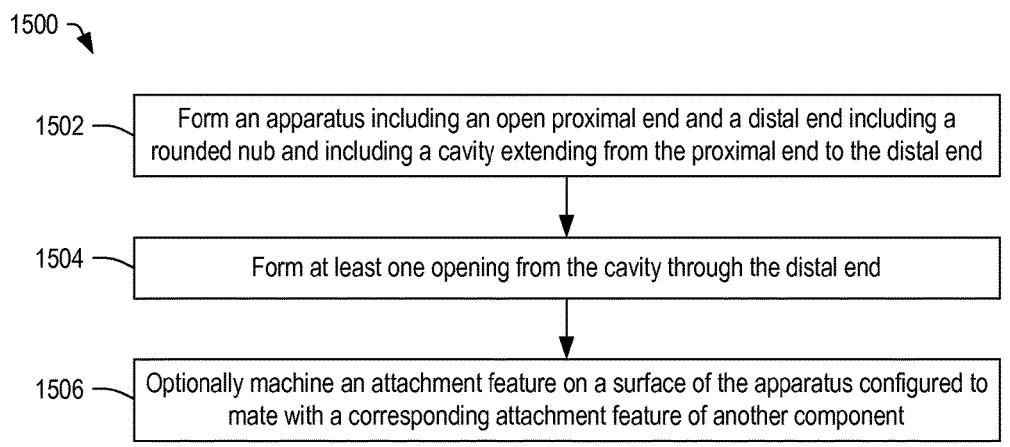
FIG. 15 is a flow diagram of a method of forming a sheath configured to receive a syringe according to some embodiments.

FIG. 15 is a flow diagram of a method 1500 of forming a sheath configured to receive a syringe according to some embodiments. At 1502, an apparatus may be formed that includes an open proximal end and a distal end including a rounded nub and that includes a cavity extending from the proximal end to the distal end. Advancing to 1504, at least one opening is formed that extends from the cavity through the distal end. Continuing to 1506, an attachment feature may be optionally machined on a surface of the apparatus configured to mate with a corresponding attachment feature of another component. In some embodiments, the apparatus may be a syringe having a nub, and the attachment feature may include a recess configured to mate with a flange or ridge on an interior surface of a cap or sheath (the other component) that also includes a nub. In some embodiments, the apparatus may be a sheath or cap that is configured to couple to a corresponding attachment feature on a syringe. In some embodiments, the sheath and the syringe may include a nub. In some embodiments, the sheath may include a nub, and the syringe may include a neck portion that extends at least partially toward the nub.

In conjunction with FIGS. 1-15, an apparatus is described that includes a distal end having a rounded nub and at least one opening. The apparatus may be a sheath, a cap, a syringe, or any combination thereof. The distal end of the apparatus may be rounded to present a blunt or "edgeless" end presenting a substantially smooth transition from an elongate portion to a distal portion of the apparatus. In some embodiments, the apparatus may be used for home-based artificial insemination, such as by insertion of the apparatus into the vagina of a woman until the nub contacts the woman's cervix. The plunger may then be depressed to expel seminal fluid onto the cervix to provide artificial insemination.

In some embodiments, the apparatus may include a syringe having a substantially tubular shape and having a substantially rounded distal end. The syringe may further include a rounded nub extending from the distal end proximate to a longitudinal axis of the syringe. In some embodiments, the rounded nub may include an opening to allow fluid to pass therethrough. In some embodiments, the distal end may include a plurality of openings to allow fluid passage.

In some embodiments, the apparatus may include a syringe and a sheath having a cavity sized to receive the syringe. The sheath may include one or more openings on a distal end that are configured to align with (or mate with) a fluid opening of the syringe. In some embodiments, the sheath may include an attachment feature configured to mate with a corresponding feature on the syringe. In an example, the attachment feature may include threads configured to mate with corresponding threads of the syringe to secure the syringe within the sheath. In another example, the attachment mechanism may include a raised edge on one of an interior surface of the sheath and an exterior surface of the syringe that is configured to mate with a corresponding recess on the other of the exterior surface of the syringe and the interior surface of the sheath. Further, in some embodiments, at least a portion of the sheath may be formed from a first material, and at least a portion of the syringe may be formed from a second material. In some embodiments, the first material may be more flexible or malleable than the second material.

In some embodiments, a cap or partial sheath may be configured to mate with a syringe to provide a rounded end having a nub and including one or more openings for fluid passage. In some embodiments, the nub may be rounded and may include an opening configured to align to an opening of the syringe to allow fluid from the syringe to pass therethrough. In some embodiments, the cap or partial sheath may include an attachment feature configured to mate with a corresponding feature of the syringe to secure the cap or partial sheath to the syringe. In some embodiments, the syringe may be formed from a first material, and the cap or partial sheath may be formed from a second material. The first material may be more rigid than the second material.

Although the present invention has been described with reference to preferred embodiments, workers skilled in the art will recognize that changes may be made in form and detail without departing from the scope of the invention.

What is claimed is:

1. An apparatus comprising:
a syringe consisting of:
a substantially cylindrical body formed from a first material and including an end portion having rounded edges and at least one opening, the cylindrical body defining a cavity and sized to fit within a woman's vagina;
a plunger sized to fit within the cavity; and
a nub formed from a second material and integrally formed with the substantially cylindrical body and extending from the end portion proximate to the at least one opening, the nub having a substantially rounded end and configured to provide tactile feedback when in contact with a cervix of the woman, the nub having a substantially hemispherical shape.

2. The apparatus of claim 1, further comprising a fastener element coupled to the substantially cylindrical body and configured to mate to a corresponding feature of the syringe.

3. The apparatus of claim 1, wherein the substantially cylindrical body includes:

a proximal end;
a distal end; and
an elongate portion extending therebetween,
wherein the distal end includes a substantially rounded corner relative to the elongate portion.

4. The apparatus of claim 1, wherein the nub includes an opening configured to align with the at least one opening of the substantially cylindrical body.

5. The apparatus of claim 1, wherein the nub comprises a substantially ring shape.

6. The apparatus of claim 1, wherein the substantially cylindrical body is sized to fit within a vaginal canal and to extend proximate to the cervix of the woman.

7. An apparatus comprising:
a syringe consisting of: a plunger;
a cylindrical body formed of a first material and having a proximal end, a distal end and an elongate portion extending therebetween, the elongate portion including an opening at the proximal end and defining a cavity sized to receive the plunger, the distal end having a rounded corner relative to the elongate portion to form a substantially smooth transition from the elongate portion to the distal end, the distal end further including an opening, the cylindrical body sized to fit within a woman's vagina; and
a nub formed of a second material and formed on and extending from the distal end proximate to the opening, the nub having a rounded end and a substantially hemispherical shape and configured to space the cylindrical body from a cervix when inserted into the woman's vagina during an artificial insemination procedure.

8. The apparatus of claim 7, wherein the nub comprises a substantially annular shape.

9. The apparatus of claim 7, wherein the nub comprises a substantially elliptical shape.

10. The apparatus of claim 7, wherein the nub includes an opening configured to align with the opening of the distal end.

11. The apparatus of claim 7, further comprising a sheath defining a cavity sized to receive the cylindrical body and including an opening configured to align to the opening of the distal end.

12. The apparatus of claim 7, wherein the cylindrical body includes an attachment element configured to mate with a corresponding attachment feature of the syringe to secure the cylindrical body to the syringe.

13. An apparatus comprising:
a syringe consisting of: a plunger;
a tubular element formed of a first material and including a body portion and a distal end and including a substantially smooth surface having rounded edges, the distal end including an opening, the body portion defining a cavity and including a plunger opening at a proximal end opposite to the distal end, the plunger opening and the cavity sized to receive the plunger, the tubular element sized to fit within a woman's vagina; and
a nub formed of a second material and formed on the tubular element and extending from the distal end proximate to the opening and having a substantially hemispherical shape, the nub configured to provide tactile feedback when in contact with a cervix of the woman.

14. The apparatus of claim 13, further comprising an attachment element configured to mate with a corresponding attachment feature of the syringe to secure the tubular element to the syringe.

15. The apparatus of claim 13, wherein the tubular element comprises a cap configured to couple to the syringe.

16. The apparatus of claim 13, wherein the nub comprises a substantially annular shape.

17. The apparatus of claim 13, wherein the nub is integrally formed with the tubular element.

18. The apparatus of claim 13, wherein the tubular element is sized to tit within a vaginal canal and to extend proximate to the cervix of the woman.

* * * * *